US00PP30315P3

(12) United States Plant Patent
Bornstein

(10) Patent No.: US PP30,315 P3
(45) Date of Patent: Mar. 26, 2019

(54) *GYPSOPHILA* PLANT NAMED 'PEARLS WHITE WISH'

(50) Latin Name: ***Gypsophila paniculata* L.**
Varietal Denomination: Pearls White Wish

(71) Applicant: Selecta Cut Flowers S.A.U., Barcelona (ES)

(72) Inventor: Menachem Bornstein, Holon (IL)

(73) Assignee: Selecta Cut Flowers S.A.U, Barcelona (ES)

( * ) Notice: Subject to any disclaimer, the term of this patent is extended or adjusted under 35 U.S.C. 154(b) by 0 days.

(21) Appl. No.: 15/731,601

(22) Filed: Jul. 6, 2017

(65) Prior Publication Data

US 2019/0014707 P1 Jan. 10, 2019

(51) Int. Cl.
*A01H 5/02* (2018.01)
*A01H 6/00* (2018.01)

(52) U.S. Cl.
USPC ..... Plt./354
CPC ..... *A01H 6/00* (2018.05); *A01H 5/02* (2013.01)

(58) Field of Classification Search
USPC ..... Plt./354
See application file for complete search history.

*Primary Examiner* — Keith O. Robinson
(74) *Attorney, Agent, or Firm* — Bethany R. Roahrig; Cochran Freund & Young LLC

(57) ABSTRACT

A new *Gypsophila* plant particularly distinguished by medium, semi-double to double flowers and an upright growth habit, is disclosed.

1 Drawing Sheet

Genus and species: *Gypsophila paniculata* L.
Variety denomination: 'Pearls White Wish'.

CROSS-REFERENCE TO RELATED APPLICATIONS

An application with the Community Plant Variety Rights Office was filed on Apr. 4, 2017. 'Pearls White Wish' has not been made publicly available or sold more than one year prior to the filing date of the instant application.

BACKGROUND OF THE NEW PLANT

The present invention comprises a new and distinct variety of *Gypsophila*, botanically known as *Gypsophila paniculata* L., and hereinafter referred to by the variety name 'Pearls White Wish'. 'Pearls White Wish' originated from an open-pollination conducted in Negev, Israel in April 2010 between the proprietary female *Gypsophila* variety 'BL-MD-F-556' (unpatented) and an unnamed and unpatented male *Gypsophila* variety.

The seeds from the cross were sown and plants were grown for evaluation, where an individual plant designated 'Pearls White Wish' was selected from the group of plants in Negev, Israel in August 2010.

In September 2010, 'Pearls White Wish' was first vegetatively propagated by side branch cuttings. 'Pearls White Wish' was found to reproduce true to type in successive generations of asexual propagation via side branch cuttings.

SUMMARY

The following are the most outstanding and distinguishing characteristics of this new variety when grown under normal horticultural practices in Negev, Israel.

1. Medium, semi-double to double flowers; and
2. An upright growth habit.

DESCRIPTION OF THE PHOTOGRAPH

This new *Gypsophila* plant is illustrated by the accompanying photograph which shows the plant's overall plant habit including form and flowers. The photograph is of a 22-week-old plant grown outdoors in Colombia in April 2016. The colors shown are as true as can be reasonably obtained by conventional photographic procedures.

DESCRIPTION OF THE NEW VARIETY

The following detailed descriptions set forth the distinctive characteristics of 'Pearls White Wish'. The data which define these characteristics were collected from asexual reproductions carried out in Juja, Kenya. Data was collected on 18-week-old plants grown outdoors in Juja, Kenya in January 2017. Color references are to The R.H.S. Colour Chart of The Royal Horticultural Society of London (R.H.S.) 2007.

Classification:
- *Family*.—Caryophyllaceae.
- *Botanical*.—*Gypsophila paniculata* L.
- *Common*.—Baby's breath.
- *Designation*.—'Pearls White Wish'.

Parentage:
- *Female parent*.—The proprietary female *Gypsophila* variety 'BL-MD-F-556' (unpatented).
- *Male parent*.—An unnamed and unpatented male *Gypsophila* variety.

Plant:
- *Form*.—Perennial, shrub type.
- *Growth habit*.—Upright.
- *Height*.—105.0 cm.
- *Width*.—85.0 cm.

*Time to produce a finished flowering plant.*—16 to 18 weeks; 4 weeks rooting and 12 to 14 weeks between planting and flowering, depending on weather and cultivation conditions.

*Propagation type.*—Vegetative, by side branch cuttings.

*Time to initiate and develop roots.*—2 weeks, fully rooted and ready for planting after 4 weeks.

*Root description.*—White to light brown, RHS 155A at root tip and RHS 162D at the base; woody main spike with branched fibrillary secondary roots.

Flowering stems:

*Number of branches per plant.*—6 to 8.

*Basal branching.*—Present.

*Stem strength.*—Stable.

*General description.*—Panicle.

*Length.*—85.0 cm.

*Diameter.*—0.5 cm to 0.8 cm at the stem base.

*Internode length.*—4.0 cm to 5.0 cm at the stem base.

*Color.*—RHS 147C (Yellow-Green).

*Texture.*—Glabrous.

Leaves:

*Arrangement.*—Opposite.

*Shape.*—Lanceolate.

*Cross section of leaf.*—Moderately concave.

*Apex.*—Acute.

*Base.*—Cuneate.

*Margin.*—Entire.

*Immature and mature leaf color, both surfaces.*—RHS 137A.

*Length.*—8.0 cm to 9.5 cm.

*Width.*—1.5 cm to 2.0 cm.

*Texture.*—Fine pubescence on both surfaces, finer at the upper surface than the lower side.

*Venation type.*—Parallel.

*Venation color, both surfaces.*—RHS 137B.

Inflorescence:

*Inflorescence type.*—Compound cymes with numerous flowers; panicles.

*Flowering season.*—Year-round; 12 hours and above light duration.

*Lastingness of individual flowers on the plant.*—10 to 12 days.

*Lastingness of the flowers as a cut flower.*—10 to 12 days.

*Flower width.*—0.7 cm to 0.8 cm.

*Flower depth.*—0.5 cm to 0.6 cm.

*Flower shape.*—Oblate consisting of many semi-double to double-type petals.

*Flower profile, upper part.*—Moderately convex.

*Fragrance.*—Faint, unpleasant smell.

*Number of inflorescences per plant.*—7 to 9.

*Number of flowers per inflorescence.*—Average between 500 and 800.

*Inflorescence pubescence.*—Absent.

*Flower buds.*—Color: RHS 155A (White). Shape: Oblate. Length: 0.3 cm to 0.4 cm. Diameter: 0.3 cm.

*Peduncle.*—Length (height): 85.0 cm. Diameter: 0.5 cm to 0.6 cm. Strength: Stable. Texture: Glabrous. Color: RHS 144A.

*Pedicel.*—Length: 0.6 cm to 0.9 cm. Diameter: 0.09 cm. Strength: Stable. Texture: Glabrous. Color: RHS 146C.

*Petals.*—Arrangement: Pompon. Quantity: 47 to 55 per flower. Shape: Spatulate. Apex: Emarginate. Base: Cuneate. Margin: Entire. Curvature of longitudinal axis of petal: Moderately recurved. Size: Length: 0.35 cm. Width: 0.15 cm. Color: When opening (both upper and lower surfaces): RHS 155A. Fully opened (both upper and lower surfaces): RHS 155D. Surface texture (both upper and lower surfaces): Glabrous.

*Sepals.*—Arrangement: Like a cup. Quantity per flower: 5 to 7. Shape: Lanceolate. Apex: Acute. Base: Cuneate. Margin: Entire. Length: 0.3 cm. Width: 0.1 cm. Color (both upper and lower surfaces): RHS 137C. Surface texture: Upper surface: Glabrous. Lower surface: Glabrous.

Reproductive organs:

*Stamens.*—Quantity per flower: 7 to 8. Anther shape: Elliptic. Anther length: 0.05 cm to 0.1 cm. Anther color: RHS 158D. Pollen amount: No pollen observed.

*Pistils.*—Quantity per flower: 1. Pistil length: 0.9 cm to 1.0 cm. Style length: 0.5 cm. Style color: RHS 181D. Stigma color: RHS 75D. Ovary color: RHS 137C.

Fruit and seed set: None observed.

Disease and pest/insect resistance: None observed.

COMPARISON WITH PARENTAL LINE AND KNOWN VARIETY

'Pearls White Wish' is distinguished from the female parent and the commercial comparison variety 'Perfecta' (patent status unknown) as described in Table 1.

TABLE 1

Comparison with Parental Line and Commercial Variety

| Characteristic | 'Pearls White Wish' | Female parent 'BL-MD-F-556' | Commercial Variety 'Perfecta' |
|---|---|---|---|
| Flower size | Medium | Large | Large |
| Flowering period | Early | Early | Late |

I claim:

1. A new and distinct variety of *Gypsophila* plant designated 'Pearls White Wish' as illustrated and described herein.

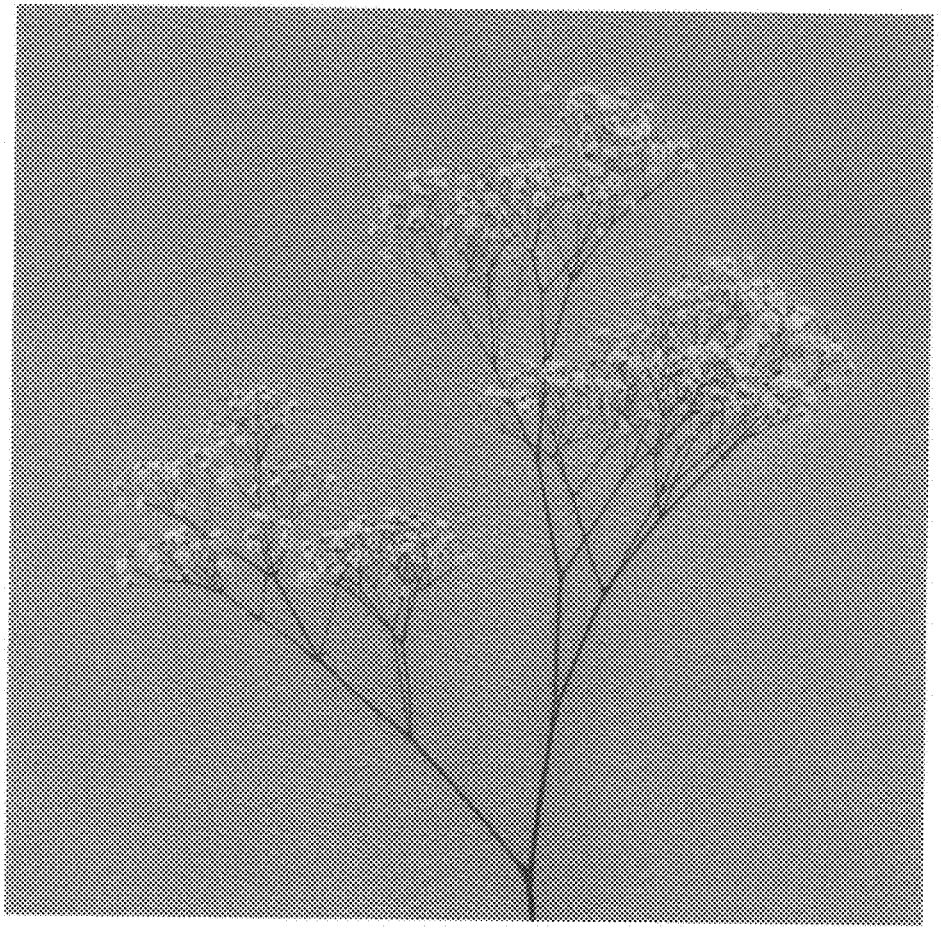

* * * * *